(12) United States Patent
Du et al.

(10) Patent No.: US 10,646,636 B2
(45) Date of Patent: May 12, 2020

(54) NEEDLE DISLODGEMENT AND BLOOD LEAKAGE DETECTION DEVICE

(71) Applicant: Southern Taiwan University of Science and Technology, Tainan (TW)

(72) Inventors: Yi-Chun Du, Tainan (TW); Bee Yen Lim, Selangor (MY); Ming-Jui Wu, Kaohsiung (TW)

(73) Assignee: SOUTHERN TAIWAN UNIVERSITY OF SCIENCE AND TECHNOLOGY, Tainan (TW)

( * ) Notice: Subject to any disclaimer, the term of this patent is extended or adjusted under 35 U.S.C. 154(b) by 339 days.

(21) Appl. No.: 15/672,311

(22) Filed: Aug. 9, 2017

(65) Prior Publication Data

US 2017/0333615 A1    Nov. 23, 2017

Related U.S. Application Data

(63) Continuation-in-part of application No. 14/558,688, filed on Dec. 2, 2014, now abandoned.

(30) Foreign Application Priority Data

Jun. 25, 2014  (TW) .............................. 103121918 A

(51) Int. Cl.
*A61M 1/36* (2006.01)

(52) U.S. Cl.
CPC ....... *A61M 1/3656* (2014.02); *A61M 2205/15* (2013.01); *A61M 2205/18* (2013.01); *A61M 2205/3313* (2013.01); *A61M 2205/3317* (2013.01); *A61M 2205/3592* (2013.01); *A61M 2205/502* (2013.01)

(58) Field of Classification Search
CPC ............ A61M 1/3656; A61M 2205/15; A61M 2205/18; A61M 2205/3317; A61M 2205/3313; A61M 2205/3592; A61M 2205/502

See application file for complete search history.

(56) References Cited

U.S. PATENT DOCUMENTS

| 2003/0216663 | A1* | 11/2003 | Jersey-Willuhn | .... A61B 5/0536 600/547 |
| 2008/0041792 | A1* | 2/2008 | Crnkovich | .............. A61F 13/42 210/739 |
| 2019/0255244 | A1* | 8/2019 | Lazar | ...................... A61M 1/14 |

* cited by examiner

*Primary Examiner* — Christine S. Kim
(74) *Attorney, Agent, or Firm* — Leong C. Lei

(57) ABSTRACT

A needle dislodgement and blood leakage detection device includes a sensor assembly having a flexible sensor and a flexible substrate. The flexible sensor is provided, on an underside thereof at a location close to the flexible substrate, with a photoelectric sensor including near infrared transmitters that are of an array arrangement. The photoelectric sensor includes a signal amplifier module and a signal filter module that are electrically connected. An alarm device is coupled to the sensor assembly and includes a microprocessor unit, which includes a digital signal converter module, a signal sampling module, a signal demodulation module, a signal processing module, a time division module, a storage module, and a wireless transmission module that are connected in series. The digital signal converter module is connected to the signal filter module. The storage module and the wireless transmission module are respectively connected to a display unit and a computer.

6 Claims, 8 Drawing Sheets

NEEDLE DISLODGEMENT AND BLOOD LEAKAGE DETECTION DEVICE

CROSS-REFERENCE TO RELATED APPLICATION

This is a continuation-in-part of co-pending U.S. patent application Ser. No. 14/558,688 filed on Dec. 2, 2014 and owned by the present applicant.

BACKGROUND OF THE INVENTION (a) Technical Field of the Invention

The present invention generally relates to a detection device, and more particularly to a needle dislodgement and blood leakage detection device that detects, instantaneously, extravasation under skin.

(b) Description of the Prior Art

Extravasation injury or blood leakage often occur after inserting and removing a needle. If the patient and medical attendants do not identify the situation timely, blooding of the patient in a large scale may happen and this may put the patient's life at risk. In view of such a problem, devices that detect blood leakage are available, such as a blood leakage detection device proposed in US Patent Application Publication No. 2008/0249487.

This known blood leakage detection device adopts a single-spot detection approach, in which a tip of an optic fiber probe may be easily shifted away due to a signal wire of the optic fiber probe being pulled and stretched so as to cause false detection and resulting in undesired delay of issuing blood leakage alarm. Further, the optic fiber probe must be arranged on the same parallel line as the needle and may thus press on the area where the needle pierces into a fistula, making it easily compress the fistula and the needle. Further, the known blood leakage detection device can only detects the leakage of blood and cannot be used to detect needle dislodgement where the needle undeservedly slides off. It also cannot issue an alarm message when the known detection device gets detached.

Thus, it is desired to have a wearable device for monitoring hypodermic extravasation information during a continuous injection therapeutic process.

The present invention aims to provide a solution that overcome the above problems.

SUMMARY OF THE INVENTION

Thus, an objective of the present invention is to provide a needle dislodgement and blood leakage detection device capable of instantaneously detecting hypodermic extravasation.

To achieve the above objective, the present invention comprises a sensor assembly and an alarm device. The sensor assembly comprises a flexible sensor and a flexible substrate. The flexible sensor is provided, on an underside thereof at a location close to the flexible substrate, with a photoelectric sensor. The photoelectric sensor comprises a plurality of near infrared transmitters, and the near infrared transmitters are of an array arrangement. The photoelectric sensor comprises a signal amplifier module and a signal filter module that are electrically connected. The alarm device is coupled to the sensor assembly. The alarm device comprises a microprocessor unit. The microprocessor unit comprises a digital signal converter module, a signal sampling module, a signal demodulation module, a signal processing module, a time division module, a storage module, and a wireless transmission module that are connected in series, wherein the digital signal converter module is connected to the signal filter module; the storage module is connected to a display unit; and the wireless transmission module is connected to a computer.

By using the liquid content volume and unoxygenated blood concentration of the skin tissue as a measurement reference, with a plurality of 760 nm-wavelength near infrared transmitters forming array type detection, with high speed switching and time division mode to realize instantaneous hypodermic extravasation detection. When the photoelectric sensor detects a scattered reflection signal, the signal is subjected to filtration and amplification through the signal amplifier module and signal filter module, followed by using an analog to digital converter (ADC) to carry out light signal demodulation in the microprocessor unit to generate a risk-level voltage level signal (AD Scale), and based on a variation of such date, liquid volume of the skin tissue can be determined. Finally, through the transmission capability of the wireless transmission module, the extravasation information is transmitted to a monitor terminal, such as a medical attendant, to serve a reference indicator.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
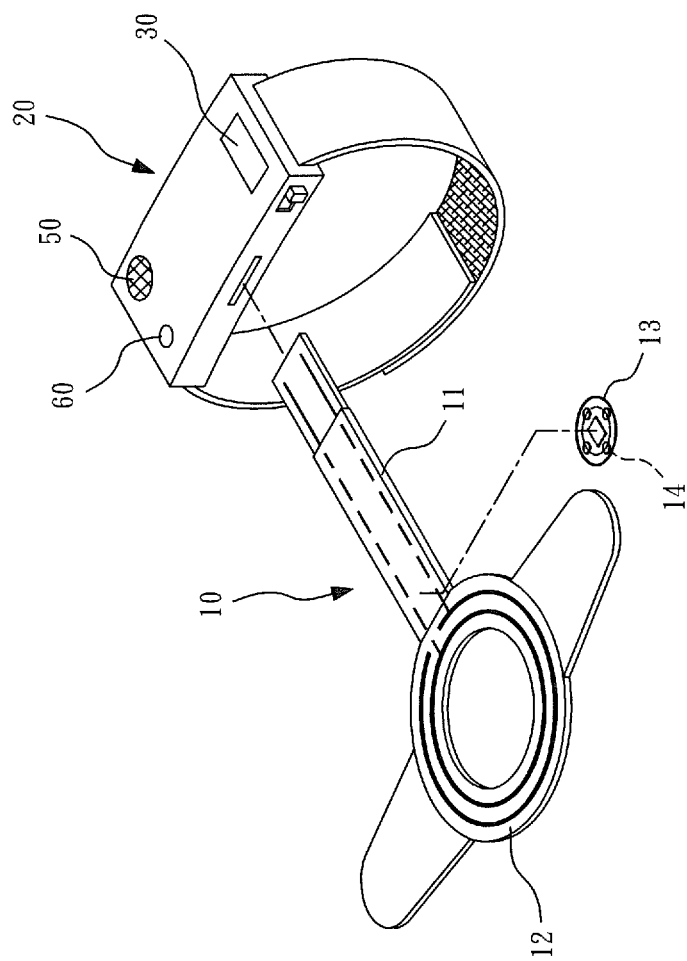
FIG. 1 is an exploded view of the present invention.
Figure 2:
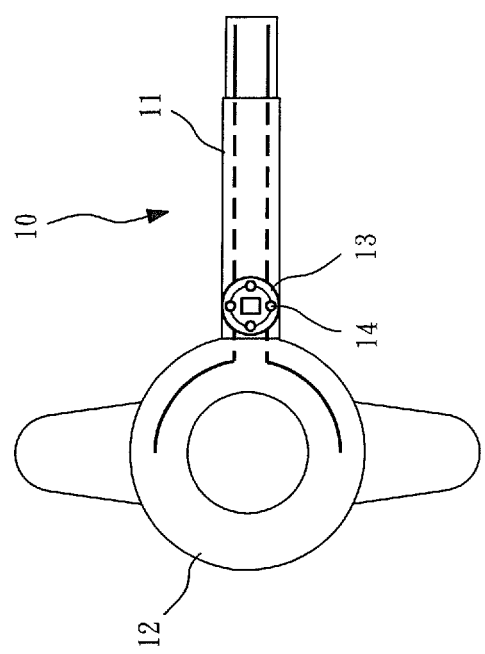
FIG. 2 is a bottom view of a sensor assembly.
Figure 3:
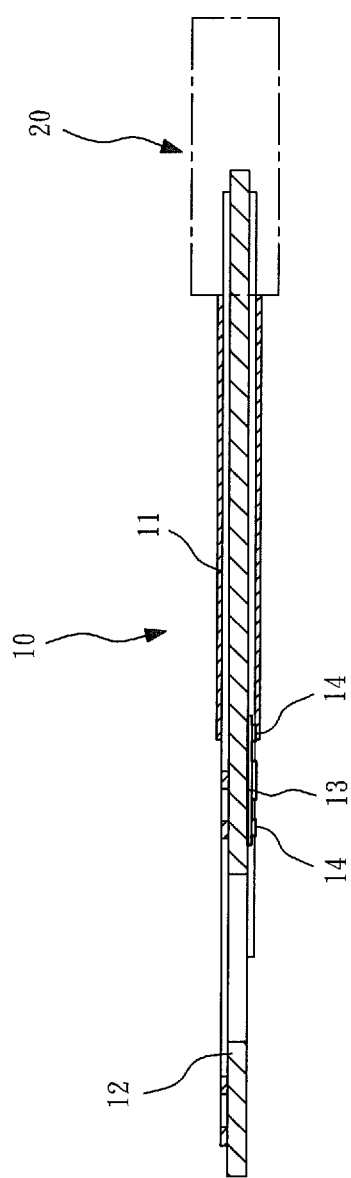
FIG. 3 is a cross-sectional view of the present invention.
Figure 4:
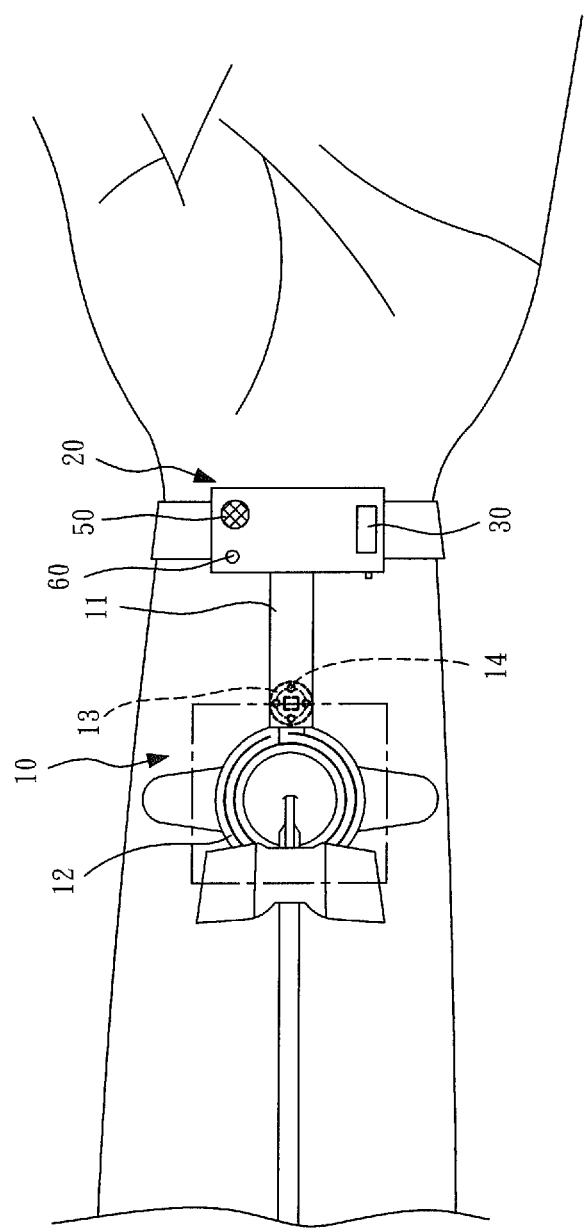
FIG. 4 is a schematic view illustrating use of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 1-4 and 9, the present invention comprises a sensor assembly 10 and an alarm device 20. Details will be provided below.

The sensor assembly 10 comprises a flexible sensor 11 and a flexible substrate 12. The flexible sensor 11 is provided, on an underside thereof at a location close to the flexible substrate 12, with a photoelectric sensor 13. The photoelectric sensor 13 comprises a plurality of near infrared transmitters 14, and the near infrared transmitters 14 are of an array arrangement. The photoelectric sensor 13 comprises a signal amplifier module 131 and a signal filter module 132 that are electrically connected.

The alarm device 20 is coupled to the sensor assembly 10. The alarm device 20 comprises a microprocessor unit 21. The microprocessor unit 21 comprises a digital signal converter module 22, a signal sampling module 23, a signal demodulation module 24, a signal processing module 25, a time division module 26, a storage module 27, and a wireless transmission module 28 that are connected in series, wherein the digital signal converter module 22 is connected to the signal filter module 132; the storage module 27 is connected to a display unit 30; and the wireless transmission module 28 is connected to a computer 40.

In one example of structure, the near infrared transmitters 14 are selected to have an adaptive spectrum having an inspection wavelength of 760 nm for hypoxia hemoglobin (HHb) and are arranged to form a circular detection area having a diameter of 2 centimeters in order to eliminate dead zones of detection that might occur in a rectangular configuration.

In one example of structure, the alarm device 20 comprises an I/O control module 29, which is operable in combination with an effective oscillator frequency to carry out fast switching of light sources at a speed of switching at each 0.3 second interval to control four channels of near infrared light sources of the near infrared transmitters 14 to provide a time division detection mode.

In one example of structure, the display unit 30 is selected as an organic light-emitting diode (OLED) display for displaying blood leakage information.

In one example of structure, the storage module 27 is connected with a buzzer 50 for giving off audio alarms.

In one example of structure, the storage module 27 is connected with a light-emitting diode (LED) alarm indicator 60 for visual alarm.

Figure 5:
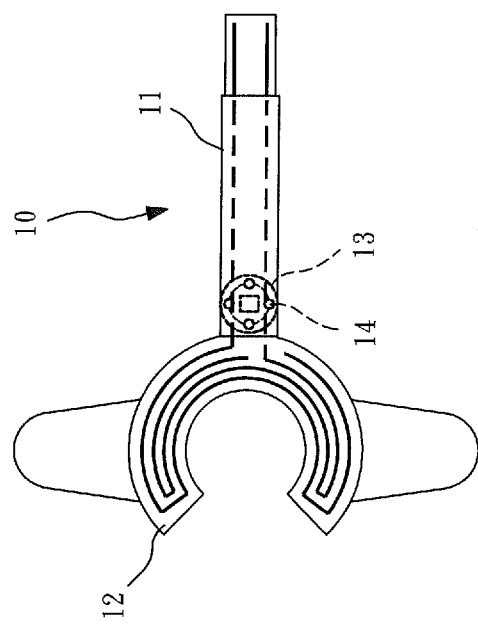
FIG. 5 is a top plan view of a sensor assembly according to a second embodiment of the present invention.
Figure 6:
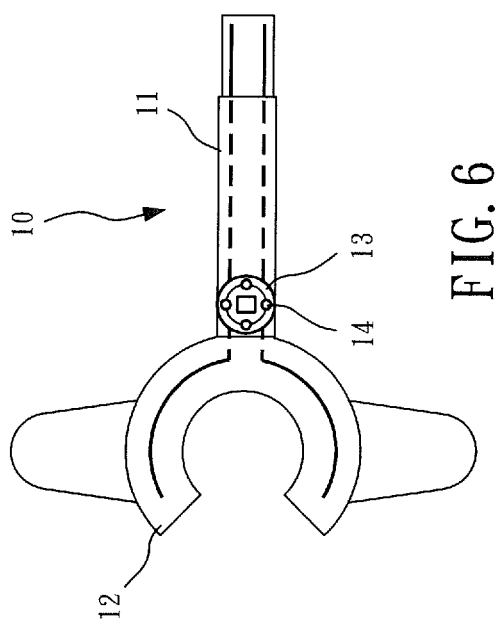
FIG. 6 is a bottom view of the sensor assembly of the second embodiment of the present invention.

Referring to FIGS. 5 and 6, an embodiment demonstrating another configuration of the sensor assembly 10 is shown.

Figure 7:
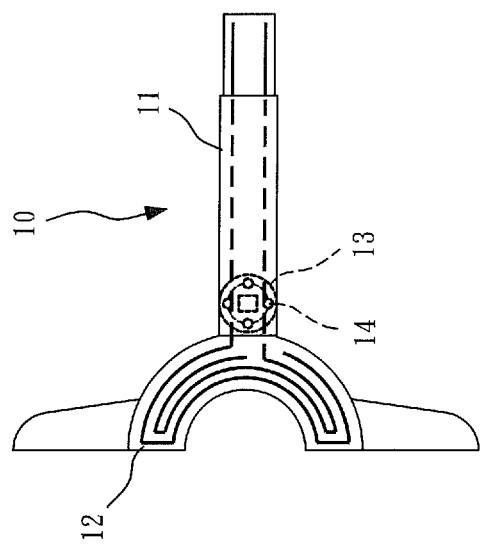
FIG. 7 is a top plan view of a sensor assembly of a third embodiment of the present invention.

Referring to FIG. 7, an embodiment demonstrating a further configuration of the sensor assembly 10 is shown.

Figure 8:
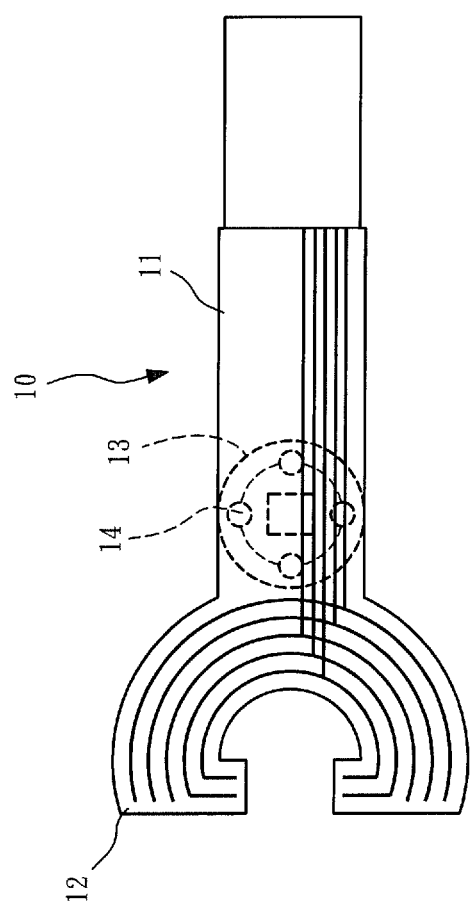
FIG. 8 is a top plan view of a sensor assembly of a fourth embodiment of the present invention.
Figure 9:
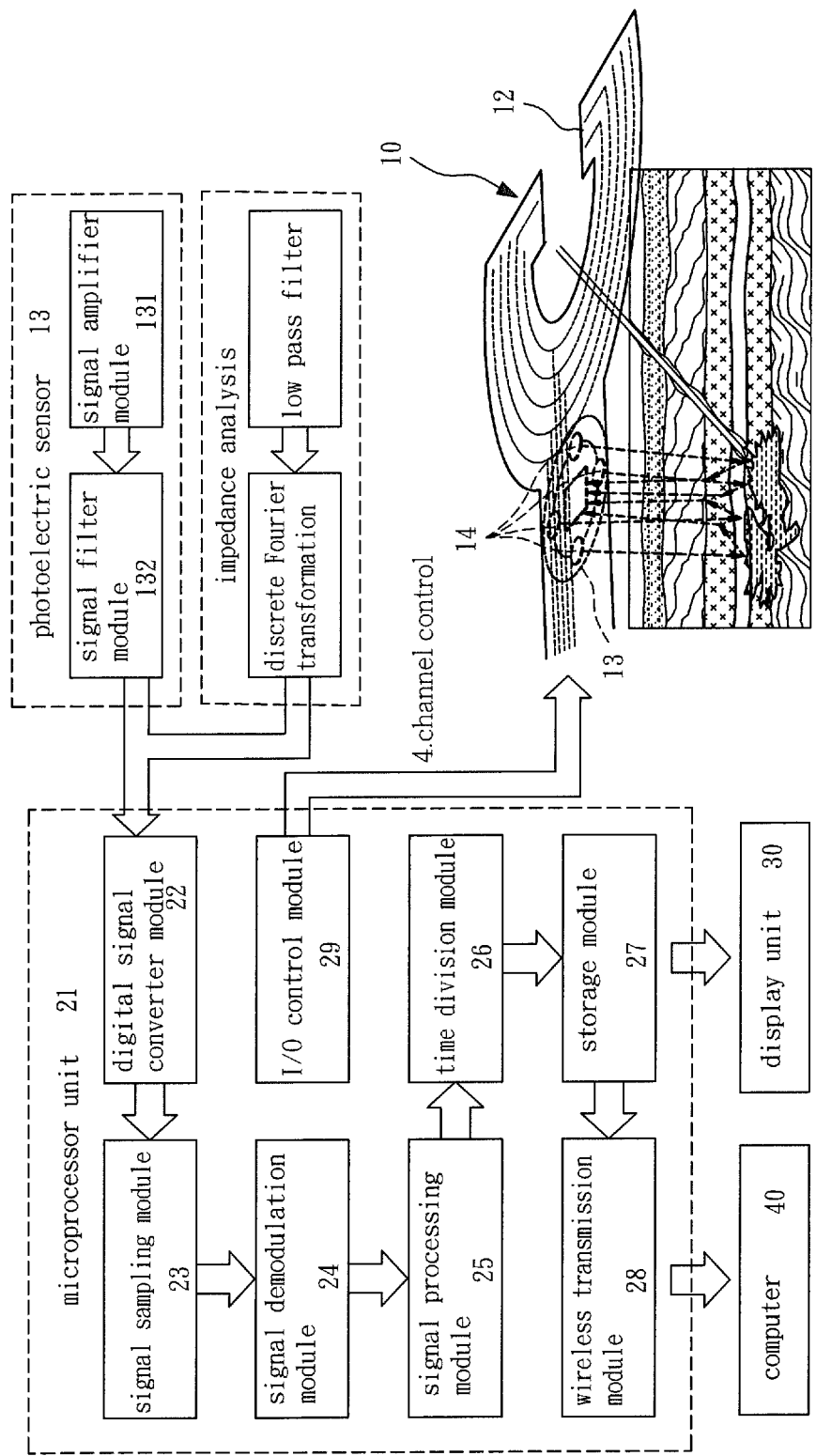
FIG. 9 is a system block diagram of the present invention.

Referring to FIG. 8, an embodiment demonstrating yet a further configuration of the sensor assembly 10 is shown.

The above provides a description to the structure of the present invention. The following provides a description to the components of the present invention and assemblies thereof, followed by a description concerning applications, features, and advantages of the present invention.

The present invention uses near infrared spectroscopy (NIRS) principle to make use of interaction of light among tissues of skin to induce variation of near infrared light energy to establish an array type near infrared hypodermic extravasation detection system.

By using the liquid content volume and unoxygenated blood concentration of the skin tissue as a measurement reference, with a plurality of 760 nm-wavelength near infrared transmitters 14 forming array type detection, with high speed switching and time division mode to realize instantaneous hypodermic extravasation detection. When the photoelectric sensor 13 detects a scattered reflection signal, the signal is subjected to filtration and amplification through the signal amplifier module 131 and signal filter module 132, followed by using an analog to digital converter (ADC) to carry out light signal demodulation in the microprocessor unit 21 to generate a risk-level voltage level signal (AD Scale), and based on a variation of such date, liquid volume of the skin tissue can be determined. Finally, through the transmission capability of the wireless transmission module 28, the extravasation information is transmitted to a monitor terminal, such as a medical attendant, to serve a reference indicator.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A needle dislodgement and blood leakage detection device, comprising:
    a sensor assembly, which comprises a flexible sensor and a flexible substrate, the flexible sensor being provided, on an underside thereof, with a photoelectric sensor, the photoelectric sensor comprising a plurality of near infrared transmitters, which are of an array arrangement, the photoelectric sensor comprising a signal amplifier module and a signal filter module that are electrically connected; and
    an alarm device, which is coupled to the sensor assembly, the alarm device comprising a microprocessor unit, the microprocessor unit comprising a digital signal converter module, a signal sampling module, a signal demodulation module, a signal processing module, a time division module, a storage module, and a wireless transmission module that are connected in series, wherein the digital signal converter module is connected to the signal filter module; the storage module is connected to a display unit; and the wireless transmission module is connected to a computer.

2. The needle dislodgement and blood leakage detection device according to claim 1, wherein the near infrared transmitters are selected to have an adaptive spectrum having an inspection wavelength of 760nm for hypoxia hemoglobin (HHb) and are arranged to form a circular detection area having a diameter of 2 centimeters in order to eliminate dead zones of detection that might occur in a rectangular configuration.

3. The needle dislodgement and blood leakage detection device according to claim 1, wherein the alarm device comprises a I/O control module, which is operable in combination with an effective oscillator frequency to carry out switching of light sources to control near infrared light sources of the near infrared transmitters to provide a time division detection mode.

4. The needle dislodgement and blood leakage detection device according to claim 1, wherein the display unit is selected as an organic light-emitting diode (OLED) display for displaying blood leakage information.

5. The needle dislodgement and blood leakage detection device according to claim 1, wherein the storage module is connected with a buzzer for giving off audio alarms.

6. The needle dislodgement and blood leakage detection device according to claim 1, wherein the storage module is connected with a light-emitting diode (LED) alarm indicator for visual alarm.

\* \* \* \* \*